United States Patent [19]

Berg

[11] 4,046,147
[45] Sept. 6, 1977

[54] SANITARY NAPKIN

[76] Inventor: Cecilia Berg, 26A S. Fogdelyckeg, Karlshamn, Sweden, S-292 00

[21] Appl. No.: 712,117

[22] Filed: Aug. 5, 1976

[51] Int. Cl.² .................. A61F 13/16; A61F 13/20
[52] U.S. Cl. ................................. 128/290 R; 128/285
[58] Field of Search ............. 128/284, 285, 290 R, 128/290 B, 290 P

[56] References Cited

U.S. PATENT DOCUMENTS

| | | | |
|---|---|---|---|
| 2,092,346 | 9/1937 | Arone | 128/290 R |
| 2,331,355 | 10/1943 | Strongson | 128/290 R |
| 3,183,909 | 5/1965 | Roehr | 128/290 R |
| 3,420,234 | 1/1969 | Phelps | 128/285 |
| 3,420,235 | 1/1969 | Harmon | 128/290 R |
| 3,491,759 | 1/1970 | Samuel | 128/290 R |
| 3,528,422 | 9/1970 | Hodas | 128/290 R |
| 3,983,873 | 10/1976 | Hirschman | 128/285 |

FOREIGN PATENT DOCUMENTS 588,689   5/1947   United Kingdom ............ 128/290 R Primary Examiner—Aldrich F. Medbery
Attorney, Agent, or Firm—Pollock, VandeSande & Priddy

[57] ABSTRACT

A sanitary napkin formed of a single blank of soft material that is folded in such a way that a hump shape having two spaced longitudinally extending slits is formed thereon, ridges forming part of said hump shape sealing in use against the appropriate body portions.

4 Claims, 4 Drawing Figures

SANITARY NAPKIN

BACKGROUND OF THE INVENTION

The present invention relates to a sanitary napkin. It is a chief object of the invention to provide a sanitary napkin which can be used in a safe way, without being completely soaked. It is a further object of the invention to provide a sanitary napkin of a correct shape which has a very great absorptive capacity and which is made in one piece to simplify manufacture. A still further object is to provide a sanitary napkin that is virtually leak-proof.

PRIOR ART

To attain similar objects different solutions have been priorly proposed. Thus, reference is made to U.S. Pat. Nos. 2,662,527 to W. G. Jacks patented Dec. 15, 1953 and 3,183,909 to W. G. Roehr patented May 18, 1965, as well as to Swiss patent specification No. 204,076 patented Apr. 15, 1959.

SUMMARY OF THE INVENTION

The improved sanitary napkin according to the invention is made of a single blank of a soft absorbent material and is formed with a longitudinally extending hump-shaped projection having softly rounded edges. The hump projection is formed partly by the both end portions of the blank having been turned up so as to have in cross section an L-shape, partly by the middle portion of the blank being folded into a U-shape having its open portion facing away from the hump projection. The U-shape is disposed between the L-shapes whereby there are defined two spaced slits longitudinally of the sanitary napkin between the three crests or ridges afforded by the hump projection. The two outer crests are higher than the middle one. The material is of double thickness in both L-shapes by reason of the folding.

DETAILED DESCRIPTION

An embodiment of the invention will now be described, by way of example, reference being had to the drawing, in which FIG. 1 is a transverse cross section view taken at the middle of the sanitary napkin;

Figure 1:
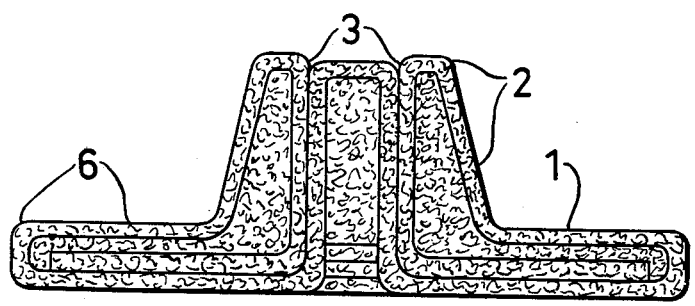

The sanitary napkin is denoted 1 in FIG. 1. The hump destined for absorption is denoted 2, having two spaced slits 3 therein.

The hump 2 is made up by folding opposite lateral portions of a napkin blank twice over, so as to form an L in cross section, and further by folding the middle portion of the blank into a U-shape having its opening facing away from the hump. The U-shaped portion is disposed between both L-shapes and extends concurrently therewith, separated from the latter by two spaced slits 3 formed in folding. Thus, the hump will have three crests or ridges of which the two outer ones are somewhat higher than the middle one.

In the position of use of the sanitary napkin the slits will become spaced farther apart whereby their softly rounded edge positions will surround the vaginal opening and will prevent soaking of the skin.

Figure 2:
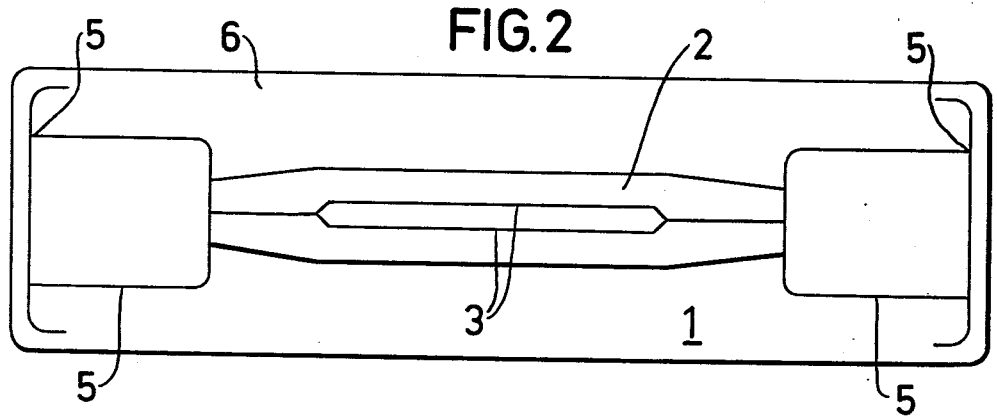
FIG. 2 is a top plan view of the napkin.
Figure 3:
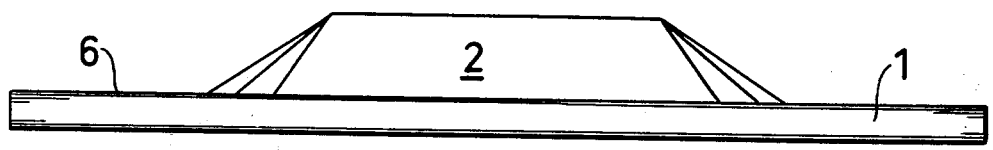
FIG. 3 is a side elevation view of the napkin.
Figure 4:
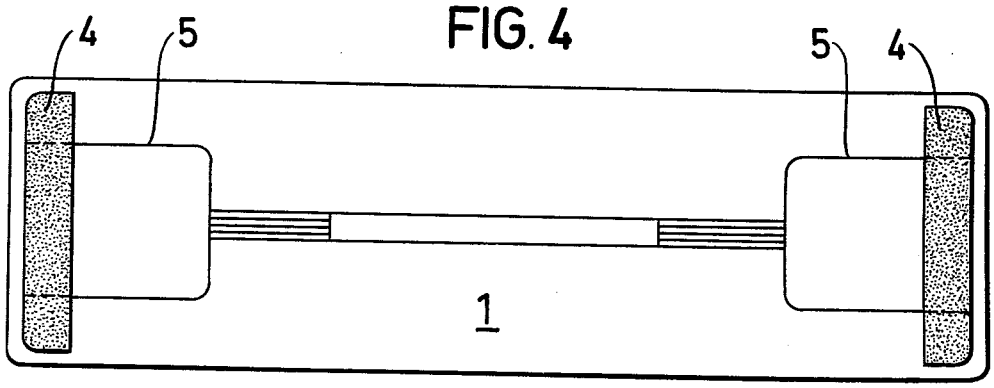
FIG. 4 is a plan view from below with the protective coating of the adhesive areas removed.

As will be evident from FIGS. 1 and 2 the sanitary napkin has a flat deck 6 with soft margins. As further seen from FIGS. 2, 3, and 4 the hump 2 at its forward and at portions merges into the flat deck. At the bottom face of the latter two adhesive pads 4 have been mounted and are held by forward and rear joints 5 of the napkin. The adhesive surfaces 4 are preferably provided with a protective coating. Before use, this protective coating is peeled off, and the napkin is made to adhere by light pressure to tight-fitting drawers.

The invention is not restricted to the embodiment shown and described, its scope of protection being defined only by the annexed claims.

What I claim is:

1. In a sanitary napkin of a soft, absorbent material and having a longitudinally extending hump portion with softly rounded edges the improvement that the napkin is manufactured of a single blank, that said hump portion if formed partly by folding opposite end portions of the blank to form in cross section an L-shape and partly by folding the middle portion of the blank to form a U-shape having its opening facing away from said hump portion, said U-shape fold being disposed between both L-shaped folds so as to define in the hump two spaced slits extending longitudinally of the napkin, said slits separating ridges cresting the hump shaped by the folded portions.

2. A sanitary napkin as claimed in claim 1 wherein the blank material has at least a double thickness at the both L-shapes by reason of its folding.

3. A sanitary napkin as claimed in claim 1, wherein both outer ridges of the hump portion are higher than the middle ridge.

4. A sanitary napkin comprising a generally flat, oblong-shaped fabric base and a projection extending longitudinally thereof for part of the length of the said base and leaving both end portions of the latter free, said projection being integral with the base and being made up of folded portions, a middle one and one lateral folded portion along each side of the middle one, said folded portions being separated by spaced slits running along the whole length thereof, the said middle portion being an inverted U-shape and the lateral portions being each an L-shape facing away from each other, the top level of said U-shape portion being lower than the top level of said L-shape portions; adhesive areas being provided at the base surface opposite said projection.

* * * * *